United States Patent [19]

Perrett et al.

[11] 4,341,206
[45] Jul. 27, 1982

[54] DEVICE FOR PRODUCING A HOLE IN A BONE

[75] Inventors: T. Robert Perrett, Wayne, Pa.; Franz Sutter, Niederdorf; Paul Gisin, Waldenburg, both of Switzerland

[73] Assignee: Synthes AG, Chur, Switzerland

[21] Appl. No.: 104,824

[22] Filed: Dec. 18, 1979

[30] Foreign Application Priority Data

Dec. 19, 1978 [CH] Switzerland ............. 12877/78
Dec. 19, 1978 [CH] Switzerland ............. 12878/78

[51] Int. Cl.$^3$ .................. A61B 17/18; A61F 5/04
[52] U.S. Cl. ...................... 128/92 EB; 128/310
[58] Field of Search ............... 128/92 EB, 310; 408/199–202, 224–225; 145/130; 131/172

[56] References Cited

U.S. PATENT DOCUMENTS

| | | | |
|---|---|---|---|
| 1,643,679 | 9/1927 | Roderick | 408/225 |
| 1,667,218 | 4/1928 | Purnis | 408/225 |
| 3,628,524 | 12/1971 | Jamshidi | 128/310 |
| 3,682,177 | 8/1972 | Ames et al. | 128/310 |
| 3,719,186 | 3/1973 | Merig, Jr. | 128/92 EB |
| 4,010,737 | 3/1977 | Vilaghy et al. | 128/310 |
| 4,076,443 | 2/1978 | Halpern | 408/202 |

FOREIGN PATENT DOCUMENTS 624108 8/1961 Italy ......................... 145/130

OTHER PUBLICATIONS

The Stanley Works, Stanley Tools Div., Screwmate ® in Popular Mechanics, May 1981, p. 228.

Primary Examiner—Kyle L. Howell
Assistant Examiner—C. W. Shedd
Attorney, Agent, or Firm—Davis, Hoxie, Faithfull & Hapgood

[57] ABSTRACT

A tool for forming a stepped blind hole in bone for receipt of a fracture reducing and stabilizing surgical implant. The tool comprises a small diameter drill portion axially adjustable with respect to a larger diameter reamer portion. A conical portion includes cutting surfaces to chamfer the entrance of the hole and also includes non-cutting portions which serve to limit penetration of the tool into the bone. The tool is cannulated to allow its use in conjunction with a previously installed Kirschner guide wire.

2 Claims, 9 Drawing Figures

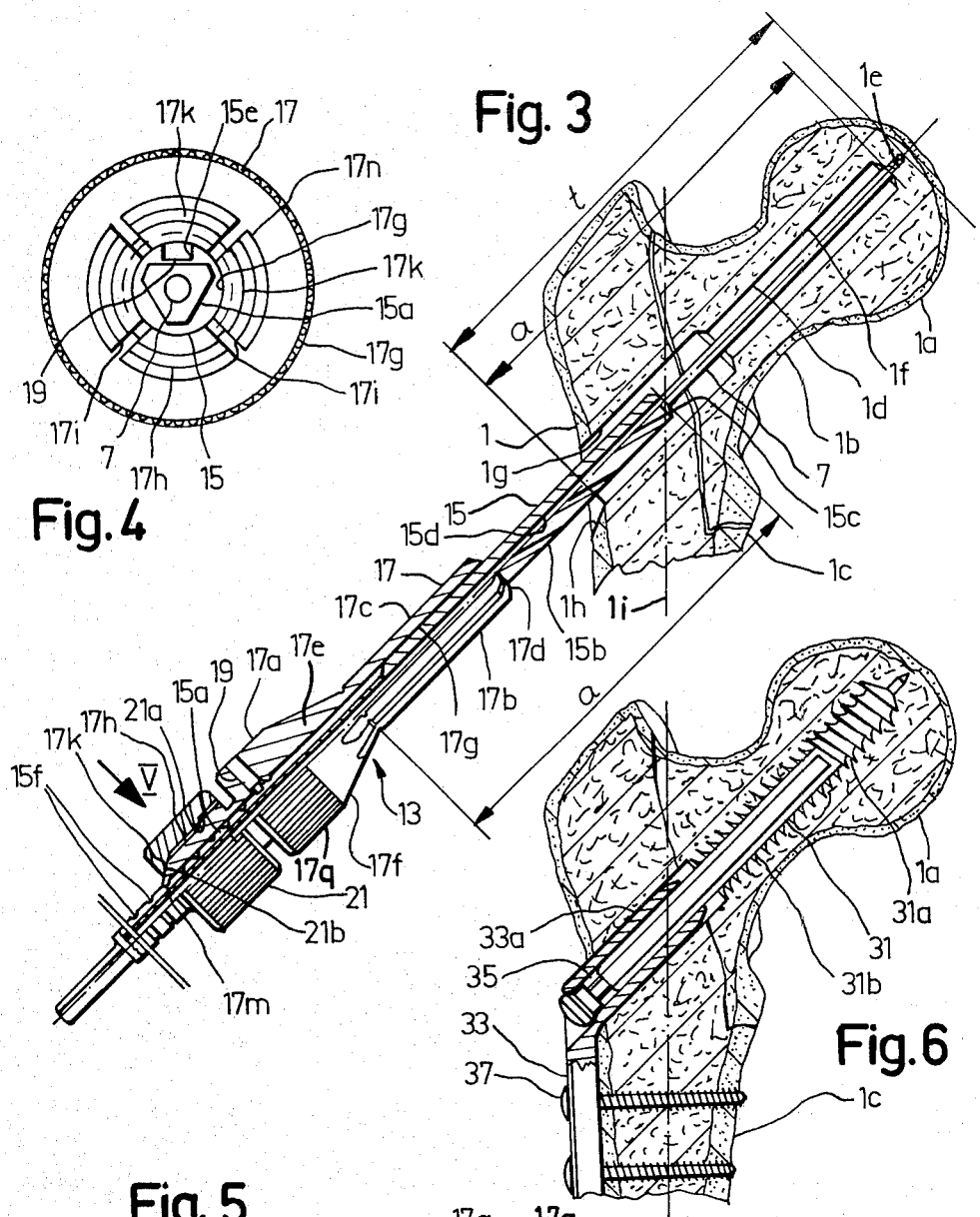

DEVICE FOR PRODUCING A HOLE IN A BONE

The present invention relates to a tool for boring a stepped hole in bone, particularly for a femur with a fracture separating the condyle. The tool produces a hole having a small cylindrical bore followed by a larger cylindrical bore followed by a conical chamfer at the surface of the bone. The portion of the tool which produces the smaller diameter cylindrical bore is retractable with respect to the portion of the tool which produces the larger diameter cylindrical bore, thereby allowing for adjustment of the depth of the smaller diameter cylindrical bore. An adjustable collet permits calibrated adjustment. The tool is cannulated with an axial bore extending throughout the length of the tool to allow the tool to be guided by a Kirschner guide wire. The portion of the tool which produces the conical chamfer at the surface of the bone includes a stop surface which is intended to limit the depth of penetration of the tool to that desired.

Surgical treatment of fractures of the neck of the thigh-bone require reduction of the fracture by means of a metallic screw implant which brings the fractured surfaces together and stabilizes the fractured surfaces in alignment for healing. The tool of the present invention has particular application to fractures of the neck of the femur, that is, fractures of the neck which connects the condyle with the major portion of the femur. The surgical implant which reduces and stabilizes the fracture comprises a lag screw which is screwed into and anchored within the condyle and a bone plate having an integral bushing through which the end of the lag screw passes. The bone plate is screwed to the major part of the femur and a small compression screw is threaded into the outer end of the lag screw. The head of the compression screw is tightened against a shouldered surface of the bone plate to draw the lag screw outwardly to reduce the fracture. Such a surgical implant is shown in U.S. Pat. No. 4,095,591.

In order to implant the lag screw, a stepped blind hole must be provided in the bone. The hole has a small diameter cylindrical section at its inner end and a large diameter cylindrical section at its outer end. The outer extremity of the hole is chamfered into a conical shape to accommodate an inwardly protruding bushing which is integral with the bone plate. The end of the lag screw is received within that bushing. The lag screw is provided with self-tapping threads which screw into the inner small cylindrical section of the hole. In order that the threaded end of the lag screw be anchored well in the condyle, it is implanted as deep as possible into the condyle but does not pass entirely through the surface of the condyle.

The length of the outer large cylindrical section of the blind hole has a diameter which is slightly greater than the exterior diameter of the bone plate bushing. The depth of the outer large cylindrical section of the hole should be somewhat greater than the length of the bushing which is received in that portion of the hole.

The stepped blind hole is produced by first installing across the fracture a Kirschner guide wire. A Kirschner wire is a long, thin rod having a self-tapping thread at its tip. The Kirschner wire is installed using an alignment device which assures that the Kirschner wire is placed at the proper angle. The Kirschner wire extends from the exterior of the femur through the bone across the fracture and into the condyle and extends nearly to the surface of the condyle.

The stepped blind hole is produced by the tool of the present invention. The tool is cannulated to allow it to slip over the previously installed Kirschner guide wire so that the Kirschner wire serves to guide the tool as the stepped hole is bored.

The Kirschner wire is installed using x-ray information to ascertain when the Kirschner wire has reached the desired position and depth. The depth of the stepped hole produced by the tool of the present invention is determined by the setting of the small diameter cylindrical bore forming portion of the tool and by the conical stop on the tool. The stepped hole bored by the tool of the present invention is assured of being at the proper angle by virtue of the proper angle of the installed Kirschner wire. When the Kirschner wire has been installed to the proper depth as ascertained by x-ray inspection, the protruding remainder of the Kirschner wire is measured with a measurement device which permits the surgeon to determine with great accuracy the appropriate length of lag screw to suit the patient. The adjustable features of the tool of the present invention assure that the stepped hole bored by the tool of the present invention is of the proper depth and configuration to suit the selected lag screw.

The tool of the present invention makes it possible for the surgeon to produce in a fractured bone, a stepped blind hole which extends at the proper angle and to precisely the correct, predetermined depth.

In the drawings;

FIG. 3 is a view in partial section through the broken femur showing the tool of the present invention in partial section and the stepped blind hole produced by the tool;

FIG. 4 is a view of the device shown in FIG. 3, shown on a larger scale, looking at the shank end of the spiral drill, the collet being omitted.

FIG. 5 is a view of a portion of the tool showing the adjustment collet which predetermines the depth to which the small diameter cylindrical boring portion of the tool extends;

FIG. 6 is a view in partial section through the broken femur showing the surgical implant installed and the fracture reduced;

Figures 1, 2:
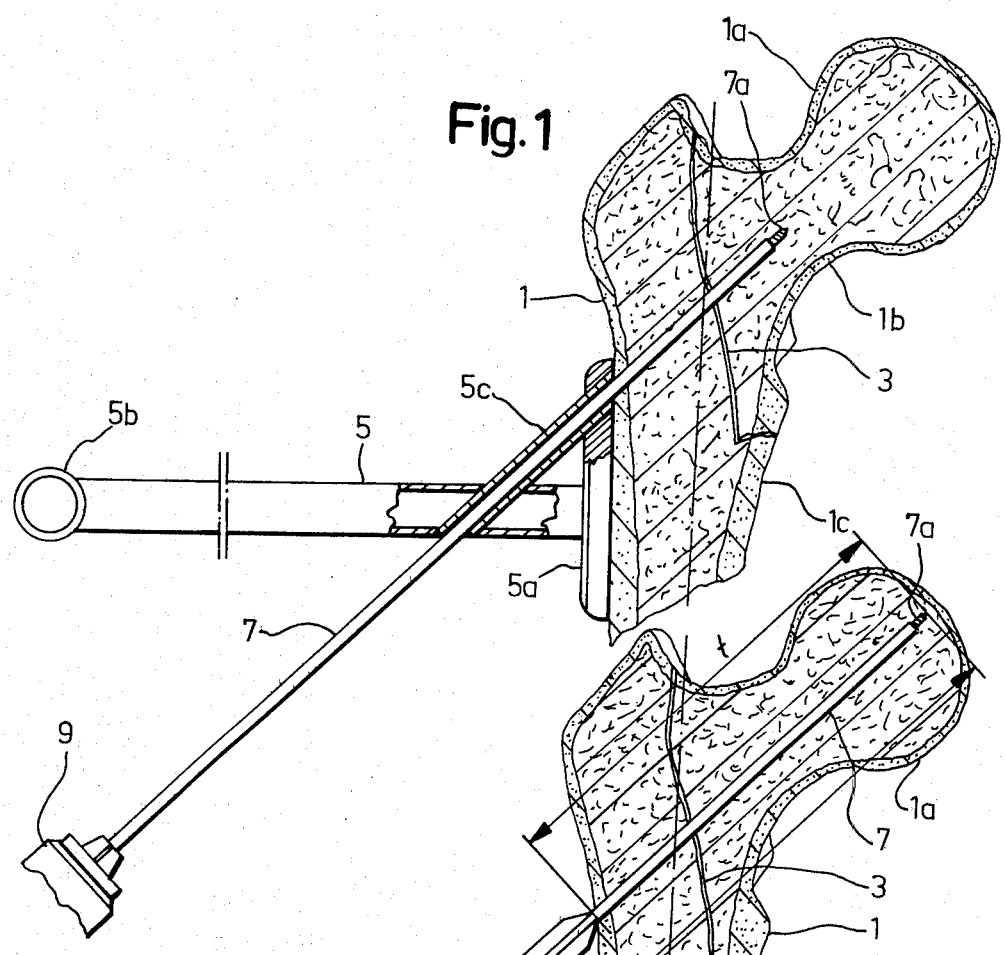
FIG. 1 is a partial section through a femur with a broken condyle showing the insertion of the Kirschner wire using a guiding device to assure the appropriate angle of entry of the Kirschner wire.
FIG. 2 is a view in partial section of the fractured femur with a Kirschner wire installed to the proper depth and showing a measurement device used to ascertain from the protruding portion of the Kirschner wire, the appropriate length of lag screw.

In FIG. 1, a femur 1 having a condyle 1-a is shown. The condyle is connected to the main portion of the femur by a neck portion 1-b. A fracture 3 is shown. At the start of the surgical operation, the bone is made accessible insofar as necessary. An alignment device 5 is placed against the main portion of the femur with a plate 5-a in contact with the bone. A handle 5-b allows the surgeon to hold the guide firmly in place against the bone. An angled guide tube or bushing 5-c has a bore of a size appropriate to receive the guide a Kirschner wire 7 having a self-tapping tip, 7-a. The Kirschner wire is driven by a chuck 9 and penetrates and threads its way through the bone across the fractured portion 3 into the condyle 1-a. Progress of the Kirschner wire as it is driven in is checked with x-ray equipment. FIG. 2 shows the Kirschner wire installed to desired depth with the tip 7-a still within the condyle 1-a. The necessary depth of the stepped hole to be bored and the length of the lag screw are ascertained by knowing the amount of the Kirschner wire which is embedded in the bone. This is measured by use of a measuring instrument 11 which is calibrated to provide a numerical reading of the amount of the Kirschner wire embedded in the bone. The calibrated scale shows the difference between the total length L of the Kirschner wire and the length of the part of the Kirschner wire which remains outside the femur. When the Kirschner wire lies in groove 11-a of the measuring instrument and the tip of the measuring instrument rests against the femur 1, the depth T of the bore hole can be read off the scale at the outer end 7-b of the Kirschner wire 7.

When the depth T is known, a stepped blind hole 1-d is drilled or bored in the femur by means of the tool 13 of the present invention, as is shown in FIG. 3. FIG. 3 shows the hole 1-d in its completed condition. The inner end of the hole is the small diameter cylindrical section 1-f. The outer portion of the hole is the large diameter cylindrical section 1-g. The mouth or entrance of the bore hole is provided with a partial conical chamfer whose surface is shown at 1-h. The axis of the blind hole 1-d extends obliquely to the main part 1-c of the femur. The small diameter cylindrical section 1-f extends through a substantial part of the condyle 1-a as well as through the neck 1-b.

The tool 13 of the present invention has a first portion in the form of a drill 15 to form the small diameter bore and a second portion in the form of a reamer 17 having cutting portion 17-b which forms the large diameter cylindrical bore. The drill portion 15 and the reamer portion 17 are relatively axially adjustable. The shank 15-a of the drill portion 15 has annular grooves 15-f and calibration marks. A collet locking device 21 shown in greater detail in FIG. 5, secures the drill portion 15 with respect to the reamer portion 17 at a desired depth of extension of the drill portion 15. The entire tool is cannulated with an axial bore 15-d to allow the tool to be guided by the previously installed Kirschner guide wire 7.

Figure 7:
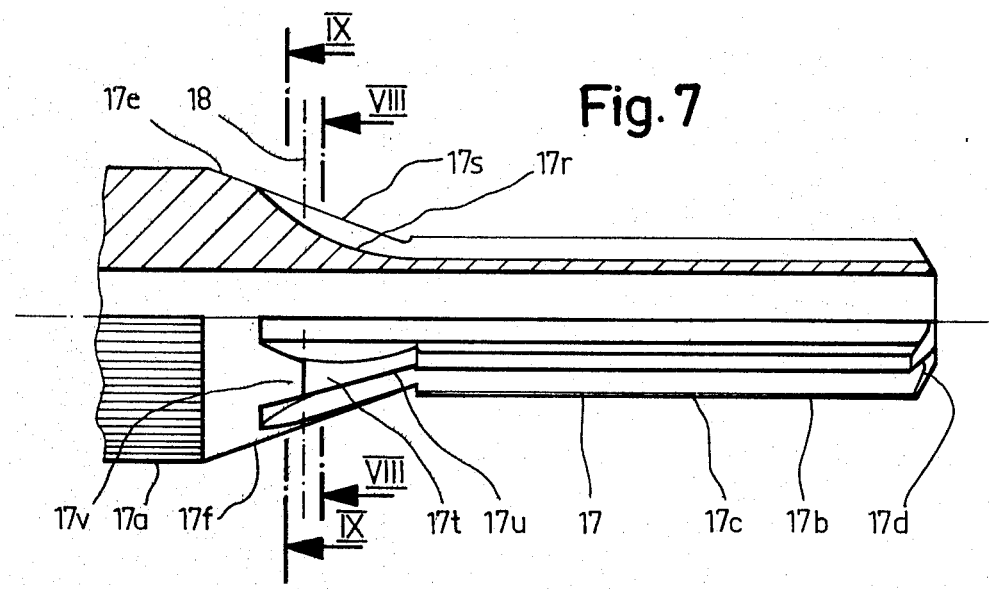
FIG. 7 is a view in partial section of that portion of the tool which bores the large diameter cylindrical hole and which forms the conical chamfer and which serves as a positive stop against undesired further penetration of the boring tool.
Figure 8:
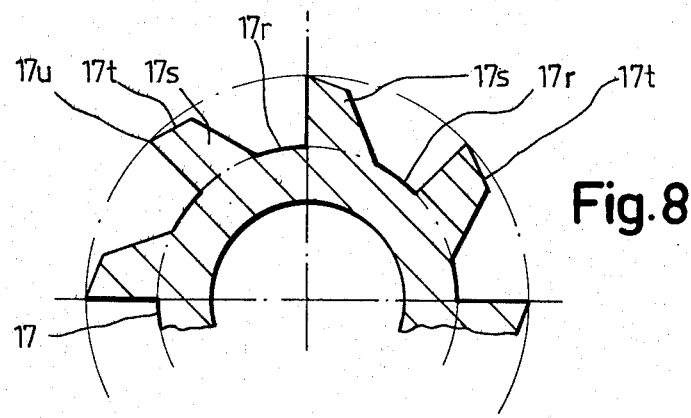
FIG. 8 is a view in section along plane VIII—VIII of FIG. 7 showing the configuration of the cutting edges for the conical chamfer forming portion of the tool.
Figure 9:
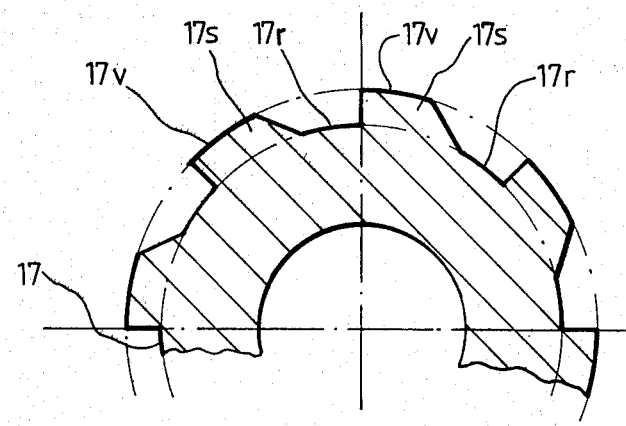
FIG. 9 is a view in section along plane IX—IX of FIG. 7 showing a further portion of the conical section of the tool which section does not perform a cutting function.

The shank 15-a of the small diameter drill portion 15 is provided with a keyway 15-e best seen in FIGS. 4 and 5 to permit slidably adjustable association with the large diameter reamer portion 17. Keyway 15-e is also provided with measurement numbers shown in FIG. 5, each of which is associated with one of the annular grooves 15-f. These measurement numbers indicate the distance a of the front end 15-c of the cutting part 15-b of the drill from the end 17-d of the large diameter cylindrical cutting tool 17. In the present example, one measurement number is provided at every second groove and the distance a can have values of between 70 and 160 mm. The large diameter bore forming tool 17 has a fastening part 17-a and a cutting part 17-b. Portion 17-b has a cylindrical section 17-c with grooves and cutting edges extending in the longitudinal direction, the cutting edges defining a cylindrical envelope surface of the large diameter bore. On the leading end 17-d of the cutting part 17-b there are provided cutting edges defining a conical envelope surface. On the end of the cylindrical section 17-c remote from the leading end 17-d there is a conical section 17-e. Conical section 17-e is provided with longitudinal grooves 17-r which are shown in FIGS. 7, 8, and 9. These longitudinal grooves of the conical section are aligned with the longitudinal grooves of the cylindrical main section 17-c and terminate in the conical surface 17-e.

Referring to FIG. 8, a section taken through plane VIII—VIII of FIG. 7 shows the form of the cutting surfaces of the conical section. Surfaces 17 are in the form of cutting flutes or ribs 17-s having a cutting edge 17-u and a rake-angled surface 17-t. The cutting edges of the large bore forming reamer portion extend from the cylindrical portion 17-c into the conical portion 17-e. As can be seen in FIG. 9, the flutes or ribs of the conical portion continue to extend in the conical portion, but are not provided with raked cutting surfaces, but form a cylindrical surface 17-v which does not perform a cutting function in the bone. On the rib 17-s present between the longitudinal groove 17-r, surfaces 17-t are ground on the outer sides of the ribs in a section which extends approximately half-way up the conical section 17-e so that the cutting edges 17-u are present only in the first half of the conical section. The rib sections present in FIG. 7 to the left of the radial plane IX are, however, no relief cut on the outside and, therefore, as can be noted in FIG. 9, are defined on the outside by surfaces 17-v of the conical surface. The sections of the ribs 17-s shown in FIG. 9, therefore, do not act as cutting edges. Further to the left of the radial plane 18 in FIG. 7, the grooves 17-r merge with the conical surface leaving an uninterrupted conical surface 17-f. Smooth conical surface 17-f and that portion of the grooved surface to the left of the radial plane 18 together form a stop surface which limits the depth of penetration of the tool into the bone. The preferred angle of the cone is between 20 and 30 degrees and most preferably is at about 27 degrees.

The reamer portion 17 of the tool is furthermore provided with a central bore 17-g to allow relative slidable positioning of the small diameter drill portion 15. The diameter of the bore 17-g is slightly greater than the diameter of the shank 15-a of the small diameter drill portion of that portion 17 is axially displaceable along the shank 15-a of the small diameter drill portion 15.

Adjoining the conical section 17-e, there is a cylindrical section 17-q through which extends a radial pin 19, which pin rides in the longitudinal groove 15-e of the shank 15-a of the drill. Thus, the tool portion 17-a is prevented from relative rotation with respect to the drill portion 15 while being permitted to move axially along the shank 15-a of the drill portion 15.

Adjoining the cylindrical section 17-q, is a detent 17-h in the form of a locking collet. The collet is in the form of a sleeve provided with a plurality of cuts 17-i parallel to the longitudinal axis of the tool so that the detent 17-h has four tongues 17-k extending in the longitudinal direction of the tool and resiliently connected with the cylindrical portion 17-q. The tongues 17-k are provided with inward protruding portions 17-m at their free ends which engage the grooves 15-f of the shank 15-a of the small diameter drill portion. An external thread 17-n engages an internally threaded member 21 which serves to lock the detent member 17-h in a preselected groove 15-f to determine the amount of extension of the small diameter drill portion 15 beyond the end 17-d of the large diameter reamer. When the threaded member 21 is screwed fast, its conical inner surface 21-b rests against the conical outer surface 17-p and presses the free tongue ends against the common longitudinal axis of the tools 15 and 17.

The production of the stepped hole 1-d will now be explained. The extension of the small diameter cylindrical drill 15 beyond the end 17-d of the large diameter reamer surface is determined by measurement with device 11 of the amount of Kirschner wire within the bone. The adjustable detent 17-h is released by unscrewing the locking collar 21 and the shank 15-a of the drill portion 15 is moved until the appropriate groove 15-f is engaged by the collet detent portion 17-m as indicated by the numerical calibrations in the keyway 15-e. The collet 21 is then screwed fast to prevent further movement of the drill portion 15 with respect to the reamer portion 17. The tool is the installed in a drill chuck 9 using the triangular driving surfaces shown in FIG. 4 to engage the jaws of the chuck. The tool is then slipped over the free end of the Kirschner wire and drilling is commenced. The Kirschner wire guides the tool precisely. The drill portion 15 first enters the bone followed by the large diameter reamer portion 17 and a stepped hole is formed. The stepped hole is bored into the bone until stop surface 17-f comes to rest against the femur 1. The tool can penetrate into the femur until the edges, lying in the radial plane 18 of the ground surfaces 17-t, come into contact with the femur. The outward ends of the groove 17-r are then still outside the femur so that the bone fragments produced upon drilling can escape through the grooves.

When the surgeon drills into the femur 1 until the stop surface comes to rest against the femur in the manner described, the total depth or length of the two cylindrical hole sections 1-f and 1-g and of the conical portion 1-h correspond to the value a. The depth a is made a few millimeters smaller than the depth t which represents the depth of the penetration of the Kirschner wire. This slight difference in depth assures that the Kirschner wire screw tip 1-e will not be unseated during the drilling operation and further assures that the lag screw, when implanted, will not penetrate the surface of the condyle. For example, if the depth t amounts to 100 millimeters and the depth a is to have a value of 95 millimeters, the tool 17 is moved along the shank 15-a of the tool 15 to a position where groove 15-f corresponding to 95 millimeters is engaged by the detent of the collet member.

Thus, the surgeon can form in the femur, in a simple and time-saving manner, a stepped blind hole 1-d whose depth a has a predetermined suitably selected value. Since the stop surface 17-f of the conical portion of the tool positively limits the maximum depth of the hole to a preselected value, a hole of the desired depth can be produced even if the conditions of the operation do not permit good visibility.

The angle between the longitudinal axis of the hole 1-d and the central axis 1-i of the femur main section 1-c in general amounts to about 30 to 50 degrees. The outer surface of the femur 1 at the mouth of the hole 1-d extends in the general direction of the central axis of the main section of the femur. The conical shape of the stop surface 17-f therefore makes it possible for the latter to come to bear against the femur 1 relatively close to the longitudinal axis of the hole 1-d. The magnitude of the angle of inclination between the axis of rotation of the tool and the central axis 1-i of the main section 1-c of the femur therefore influences the depth a of the hole relatively little.

When the femur has been provided with the hole 1-d, a lag screw 31 (shown in FIG. 6), which has a self-drilling and self-tapping thread 31-a and a shank 31-b, is screwed into the femur 1. The thread 31-a cuts into the small diameter cylindrical portion 1-f of the hole. The shank 31-b is smaller than the outside diameter of the thread 31-a and has approximately the same diameter as the small cylindrical section 1-f of the hole. The screw 31 is so selected from a set of graduated lengths that its length is approximately equal to the depth a of the hole.

The lag screw 31 is cannulated with an axial bore so that the lag screw can be installed while the Kirschner guide wire 7 is still located in the femur 1. This assures that the lag screw will be guided by the previously installed Kirschner wire. After the screw thread 31 is firmly anchored in the condyle 1-a, the Kirschner wire 7 is removed. A plate 33 having a bushing 33-a is then placed on the surface of the main part 1-c of the femur. The bushing 33-a has a slightly smaller diameter than the large diameter cylindrical hole section 1-g and is somewhat shorter than the latter is deep. The bushing 33-a is slipped over the shank of the lag screw 31 and into the large diameter hole section 1-g. The plate 33 is fastened by screws 37 to the main part 1-c of the femur 1. The outer end of the lag screw 31 is provided with a threaded hole and the bushing 33-a is provided with an internal shoulder. A compression screw 35 is then screwed into the threaded hole of the lag screw so that the head of the compression screw 35 comes to rest against the shoulder of the bushing. By tightening the compression screw 35, the pieces of the bone are pulled together so that they rest against each other at the fracture surface under compression.

We claim:

1. A tool for forming a stepped hole of controlled depth in bone for receiving a fracture reducing and stabilizing implant, comprising a twist drill, having a shank, for forming a small diameter cylindrical bore, means for forming a large diameter bore, the shank of said twist drill being slidable through said large diameter bore forming means so as to be axially extendable therefrom, means for adjusting the extent to which the twist drill extends beyond said large diameter bore forming means and a conical section abutting and tapering outwardly from said means for forming a large diameter bore on the side of said means opposite to that from which the twist drill extends, the part of said conical section nearest said large diameter bore forming means having a series of flutes and grooves, said flutes forming cutting means for chamfering the edge of the large diameter bore in the bone, the remainder of said conical section having an outer surface serving as a stop for said tool.

2. The tool claimed in claim 1 and comprising tool guiding means including a cannula extending through and concentric with the means for forming a large diameter bore and the twist drill, for receiving a guide wire anchored in the bone at the proposed location of the stepped hole.

* * * * *